United States Patent [19]

Ovyn et al.

[11] Patent Number: 6,110,681
[45] Date of Patent: Aug. 29, 2000

[54] PRIMERS AND PROBES FOR THE AMPLIFICATION, DETECTION AND TYPING OF *MYCOPLASMA PNEUMONIAE*

[75] Inventors: Caroline Louise Lucienne Ovyn, Kortrijk, Belgium; Bob van Gemen, Boxtel; Dianne Arnoldina Margaretha Wilhelmina van Strijp, Den Bosch, both of Netherlands

[73] Assignee: Akzo Nobel N.V., Arnhem, Netherlands

[21] Appl. No.: 09/125,324

[22] PCT Filed: Feb. 25, 1997

[86] PCT No.: PCT/EP97/00911

§ 371 Date: Aug. 27, 1998

§ 102(e) Date: Aug. 27, 1998

[87] PCT Pub. No.: WO97/32036

PCT Pub. Date: Sep. 4, 1997

[30] Foreign Application Priority Data

Feb. 28, 1996 [EP] European Pat. Off. ............. 96200516

[51] Int. Cl.[7] .............................. C12Q 1/68; C12P 19/34; C07H 21/04
[52] U.S. Cl. ........................... 435/6; 435/91.2; 536/24.3; 536/24.32; 536/24.33
[58] Field of Search ............................... 536/24.3, 24.32, 536/24.33; 435/91.2, 6

[56] References Cited

U.S. PATENT DOCUMENTS 5,401,631  3/1995  Lane et al. ................................... 435/6
5,459,062  10/1995  Jones et al. ........................... 435/252.1
5,552,279  9/1996  Weisberg et al. ........................... 435/6
5,656,427  8/1997  Hammond et al. ......................... 435/6

FOREIGN PATENT DOCUMENTS 0 250 662  1/1988  European Pat. Off. .
88/03957  6/1988  WIPO .

OTHER PUBLICATIONS

Okazaki et al., *Infectious Diseases*, 69:6:723–728, 1995.

Jacobs et al., *European Jornal Clinical Mirobiol.*, 15:1:38–44, 1996.

Van Kuppeveld et al., *European Journal Clin. Mirobiol. Infect. Dis.*, 13:5:401–405, 1994.

Ursi et al., *Journal of Clinical Microbiology*, 32:11:2873–2875, 1994.

Kievits et al., *Journal of Virological Methods*, 35:273–286, 1991.

Tjhie et al., *Journal Clinical Microbiology*, 32:1:11–16, 1994.

*Primary Examiner*—Kenneth R. Horlick
*Attorney, Agent, or Firm*—Michael G. Sullivan

[57] ABSTRACT

The present invention provides oligonucleotides that can be used as primers to amplify a region of the 16S rRNA of *M. pneumoniae*. Also provided are probes and kits for detection of amplified RNA and typing of *M. pneumoniae* strains. The primers, probes, methods and kits are useful for diagnosing *M. pneumoniae*.

20 Claims, 2 Drawing Sheets

1 2 3 4 5 6 7 8 9 10 11 12 13 14 15 16 17 18 19 20 21 22 23 24 25 26

1 2 3 4 5 6 7 8 9 10 11 12 13 14 15 16 17 18 19 20 21 22 23 24 25 26

PRIMERS AND PROBES FOR THE AMPLIFICATION, DETECTION AND TYPING OF *MYCOPLASMA PNEUMONIAE*

FIELD OF THE INVENTION

The present invention is directed to oligonucleotides that can be used as primers to amplify a region of the 16S rRNA of *Mycoplasma pneumoniae*. The amplified RNA can be detected with known probes for *M. pneumoniae*. However, with specific probes according to the present invention, not only detection of the amplified RNA but also further characterization with respect to the typing of *M. pneumoniae* strains is possible.

The primers, probes, methods and kits are especially useful as an aid in the diagnosis of *M. pneunoniae*.

BACKGROUND OF THE INVENTION

*Mycoplasma pneumoniae* is the causative agent of primary atypical pneumonia and is also responsible for other respiratory syndromes such as bronchitis, bronchiolitis, pharyngitis, croup and less severe upper respiratory tract infections with the highest incidence among school children.

Current methods for the diagnosis of *M. pneumoniae* infection include isolation of the organisms on complex media or demonstration of seroconversion during convalescent phases of infection (Leith et al., J. Exp. Med. 157:502–514 (1983)). The mycoplasmas, such as *Mycoplasma pneumoniae*, are fastidious organisms, requiring complex culture media containing peptone, yeast extract, expensive animal sera, and sterol. Growth is relatively slow and reaches low cell densities compared to most bacteria. In addition, atmospheric conditions for cell growth requires the addition of carbon dioxide. For these reasons, many clinical laboratories are unable to perform culture isolation of *M. pneumoniae*, and consequently are left with no real ability to diagnose the presence of this important pathogenic bacterium. Given that mycoplasmas lack cell walls, antibiotics that target the bacterial cell wall, such as penicillin, have no anti-mycoplasma activity.

Consequently, it is of importance for a physician to make a diagnosis of atypical pneumonia and prescribe the appropriate antibiotic. Initiation of appropriate therapy cannot be based on culture or serology.

Detection of genomic sequences have been proposed as rapid and specific alternatives. Different PCRs for the detection of *M. pneumoniae* have been described, using as targets the gene coding for the P1 adhesion protein (Jensen et al., Acta Pathol. Microbiol. Immunol. Scand. 97:1046–1048 (1989); Ursi et al., Acta Pathol. Microbiol.Immunol. Scand. 100:635–639 (1992)) or the 16S rRNA gene (van Kuppeveld et al., Appl. Environ. Microbiol. 58:2606–2615 (1992)) or a DNA sequence specific for *M. pneumoniae* selected from a genomic library (Bernet et al., J. Clin. Microbiol., 27:2492–2496 (1989)).

Although these methods have lesser drawbacks than culturing and serology, they are still too complex to be carried out in a routine diagnostic laboratory. False negative PCR results are rather common due to inhibitors of the PCR reaction in the clinical specimen, while false-positive results may occur due to contamination of the reagents with target DNA (Razin, Mot. and Cell. Probes, 8, 497–511 (1994)).

Based on sequence divergency of the major cytadhesin gene P1 (Su et al., Infect. Immun. 58:2669–2674 (1990)), restriction enzyme fingerprinting of genomic DNA (Su et al., J. Gen. Microbiol. 137:2727–2732 (1991); Su et al, J. Clin. Microbiol. 28:1538–1540 (1990)), two-dimensional gel electrophoresis of total proteins and PCR-mediated DNA fingerprinting (Ursi et al., J. Clin. Microbiol. 32:2873–2875 (1994)), only two types are presently recognized, indicating that *M. pneumoniae* as a species is genetically remarkably stable.

It was suggested by Ursi and coworkers that a switch in time from one type to another could be explained by the immune status of the population against one of these two types.

Typing *M. pneumoniae* is of major importance because unambiguous characterization is the basis for further identification of *M. pneumoniae* strains. Studies based on virulence differences between one strain and the other strain could be based on type-specificity. Furthermore, a relation may exist between type and sensitivity to antibiotics like macrolides and tetracyclines. Also the spread of *M. pneumoniae* strains could be studied based on type differences. The prevalence of both types seems to be time and geographic dependent.

*M. pneumoniae* has a very small genome of approximately 720–750 kb. In Mycoplasmal 16S ribosomal RNA, there are regions with highly conserved sequences and variable regions, V1 to V9, according to the nomenclature of Neefs et al. (Nucleic Acids Res. 18 suppl:2237–2317 (1990)).

Ribosomes are of profound importance to all organisms because they serve as the only 25known means of translating genetic information into cellular proteins, the main structural and catalytic elements of life. A clear manifestation of this importance is the observation that all cells have ribosomes.

Bacterial ribosomes contain three distinct RNA molecules which, at least in *Escherichia coli*, are referred to as 5S, 16S and 23S rRNAs. In eukaryotic organisms, there are four distinct rRNA species, generally referred to as 5S, 18S, 28S, and 5.8S. These names historically are related to the size of the RNA molecules, as determined by their sedimentation rate. In actuality, however, ribosomal RNA molecules vary substantially in size between organisms. Nonetheless, 5S, 16S, and 23S rRNA are commonly used as generic names for the homologous RNA molecules in any bacterium, including the mycoplasmas, and this convention will be continued herein.

An amplification system that has significant advantages over PCR amplification systems is the amplification system referred to as NASBA (nucleic acid sequence-based amplification). The NASBA methodology is disclosed in European Patent No. 0 329 822 B1. As compared to PCR, NASBA requires less user participation and fewer manipulations and steps. Another advantage is that NASBA is performed at a relatively constant temperature, ensuring that the enzymes used in the process do not lose their activity. Finally, in NASBA each cycle of the amplification process generates a plurality of RNA copies from one substrate. Therefore, it is considered preferable to use the NASBA system to amplify mycoplasmal RNA, which in turn can be detected using nucleic acid probes.

NASBA is an enzymatic process for the amplification of RNA. Four enzyme activities are required: RNA-directed DNA-polymerase, DNA-directed DNA-polymerase, RNase H and DNA-directed RNA-polymerase. The first three activities can be provided by reverse transcriptase (preferably avian myoblastosis virus reverse transcriptase (AMV-RT)), the fourth one preferably by T7 RNA-polymerase. For optimum amplification, more RNase H activity than provided by the AMV-RT can be desirable, in which case additional enzyme (e.g. *E. coli* RNase H) can be added to the reaction. The first step in NASBA consists of specific hybridization of a DNA primer to the RNA target followed by cDNA synthesis by RT. RNase H activity and annealing of a second primer allow synthesis of double-stranded DNA. One (or both) of the primers contain, in addition to target-specific hybridization sequences, an RNA polymerase promoter sequence (preferably for T7 RNA polymerase). Formation of a double-stranded RNA polymerase promoter suffices to initiate transcription by RNA-polymerase, resulting in multiple copies of the complementary RNA sequence (complementary to the original RNA sequence), which in turn can serve as target for a new round of NASBA amplification.

Variations in the NASBA method are considered within the scope of the present invention. For instance, one may use 'destabilizing' nucleotide triphosphates in the amplification, such as ionosine triphosphate disclosed in European patent application No. 92.202.564.8, published in 1994. In addition, it is not necessary to use RNase H, as a separate enzyme, in the NASBA reaction, because it is known in the art that reverse transcriptase itself has RNase H activity under appropriate conditions, as disclosed by Sambrook et al., Molecular Cloning (1993). Other variations would be apparent to those skilled in the art.

The NASBA technique applied can be followed by a detection method like 'in solution' hybridization in an enzyme-linked gel assay (ELGA) disclosed in U.S. Pat. No. 5,482,832. However, other methods can also be applied.

As in any amplification system, one must find suitable primers to amplify the sequence of interest. The need therefore exists for primer sets and hybridization probes that can be used for the amplification and subsequent detection of Mycoplasmata, particularly *Mycoplasma pneumoniae*.

SUMMARY OF THE INVENTION

The present invention is directed to oligonucleotides to be used as primers for amplification of *M. pneumoniae* 16S ribosomal RNA preferably by the NASBA® system. These primers, which can be completely described by chemical composition and structure, are single stranded DNA. A pair of primers, with each individual primer being unique, is required in the NASBA® system.

The sensitivity and reliability of *M. pneumoniae* nucleic acid sequence detection is greatly dependent on primer selection, since there is sequence variation among strains of *M. pneumoniae*. Ideally, primer selection should be based on knowledge of interstrain variability in candidate primer sequences and the consequences of mismatching at primer sites. (Chou S., J. of Clin. Microbiol., 2307–2310 (1992)).

The need therefore exists for suitable oligonucleotides including nucleic acid sequences that can be used as primers and hybridization-probes for the amplification and subsequent detection of all strain variants of *M. pneumoniae*.

The binding sites of preferred primers according to the present invention are located in a highly conserved region and a variable region (V2) of 16S ribosomal RNA.

DETAILED DESCRIPTION OF THE INVENTION

An object of the present invention is an oligonucleotide, 10–35 nucleotides in length comprising, at least a fragment of 10 nucleotides of a sequence selected from the group consisting of:

(P1) 5' AGG TCC TTT CAA CTT TGA TTC A 3' [SEQ ID NO:1], (P2) 5' GAT CCT GCC TCA GGA TTA A 3[SEQ ID NO:2], or its complementary sequence.

A preferred embodiment of the oligonucleotide according to the present invention is an oligonucleotide operably linked to a promoter nucleic acid sequence like T7 RNA polymerase with sequence 5' AAT TCT AAT ACG ACT CAC TAT AGG G 3' [SEQ ID NO: 6].

Another object of the present invention is a pair of oligonucteotide primers for the amplification of *Mycopiasma pneumoniae* nucleic acid comprising oligonucleotides consisting essentially of the following nucleic acid sequences:

(P1) 5' AGG TCC TTT CAA CTT TGA TTC A 3' [SEQ ID NO:1], (P2) 5' GAT CCT GGC TCA GGA TTA A 3' [SEQ ID NO:2], optionally linked to a promoter nucleic acid sequence.

The term "oligonucleotide" as used herein refers to a molecule comprising two or more deoxyribonucleotides or ribonucleotides such as primers and probes.

The oligonucleotides according to the present invention are highly suitable for use as primers in amplification reactions for the amplification, and subsequent detection, of mycoplasmal nucleic acid.

The term "primer" as used herein refers to an oligonucleotide either naturally occurring (e.g. as a restriction fragment) or produced synthetically, which is capable of acting as a point of initiation of synthesis of a primer extension product which is complementary to a nucleic acid strand (template or target sequence) when placed under suitable conditions (e.g. buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least about 10 nucleotides in length of a sequence substantially complementary (P1) or homologues (P2) to the target sequence, but somewhat longer primers are preferred. Usually primers contain about 15–26 nucleotides but longer primers, up to 35 nucleotides may also be employed.

Normally a set of primers will consist of at least two primers, one 'upstream' and one 'downstream' primer which together define the amplificate (the sequence that will be amplified using said primers).

An upstream primer (P1) will always contain a sequence substantially complementary to the target sequence to which it may anneal. A downstream primer (P2) will contain a sequence substantially homologues to the target sequence.

A primer may, optionally, also comprise a promoter sequence. The term "promoter sequence" defines a region of a nucleic acid sequence that is specifically recognized by an RNA polymerase that binds to a recognized sequence and initiates the process of transcription by which an RNA transcript is produced. In principle any promoter sequence may be employed for which there is a known and available polymerase that is capable of recognizing the initiation sequence. Known and useful promoters are those that are recognized by certain bacteriophage RNA polymerases such as bacteriophage T3, T7 or SP6.

It is understood that a nucleic acid primer consisting of the sequences of the present invention may contain minor deletions, additions and/or substitutions of nucleic acid bases, to the extent that such alterations do not negatively affect the yield or product obtained to a significant degree.

Various techniques for amplifying nucleic acids are known in the art. One example of a technique for the amplification of a DNA target segment is the so-called "polymerase chain reaction" (PCR). With the PCR technique the copy number of a particular target segment is increased exponentially with a number of cycles. In each cycle a DNA primer is annealed to the 3' side of each strand of the double stranded DNA-target sequence. The primers are extended with a DNA polymerase in the presence of the various mononucleotides. The extension products are rendered single stranded by thermal denaturation and each strand can serve as a template for primer annealing and subsequent elongation in a following cycle. The PCR method has been described in Saiki et al. (Science 230, 135 (1985)) and in European Patent nos. EP 0 200 362 and EP 0 201 184.

Another technique for the amplification of nucleic acid is the so-called transcription based amplification system (TAS). TAS employs an RNA-transcript-production step from a DNA, synthesized to incorporate a segment of the target sequence and a promoter, to enable transcription from the segment of a RNA with the sequence complementary to that of the target. Multiple cycles can be carried out as the RNA made in the transcription step can serve as template for making similarly transcribable DNA, which in turn, can be transcribed to yield additional RNA. The TAS method is described in International Patent Appl. no. WO 88/10315.

Yet another method for the amplification of nucleic acid is the nucleic acid sequence based amplification process ("NASBA") as described in European Patent No. 0 329 822 B1. Like TAS, NASBA includes a RNA-transcript production step using T7 RNA polymerase to transcribe multiple copies of RNA from a DNA template including a T7 promoter sequence.

It is contemplated that amplification may involve another process either in addition to or in place of the one generally illustrated in FIG. 1. These other processes, of which some are described above, using the oligonucleotides according to the present invention fall within the scope of the present invention.

There is, a priori, no known method of prediction the usefulness of a primer pair in an amplification system. Knowledge of the chemical composition and structure of primers is not sufficient to allow prediction of their usefulness in an amplification system, including NASBA.

An object of the present invention is directed to primer combinations, P1 (for instance P1 includes a T7 RNA polymerase promoter sequence (small characters)) and P2, that are useful for the amplification of a *M. pneumoniae* 16S rRNA sequence by NASBA.

P1 (OT2157): 5' aat tct aat acg act cac tat agg gAG GTC CTT TCA ACT TTG ATT CA 3' [SEQ ID NO:2]

P2 (OT2156): 5' GAT CCT GGC TCA GGA TTA A 3' [SEQ ID NO:2]

P1 primer (OT2157), initially hybridizes to the RNA template and serves as a primer for reverse transcriptase to initiate first strand cDNA synthesis. P2 primer (OT2156), which consists of a single region that hybridizes to the complementary strand of the RNA sequence to be amplified. After second strand synthesis, the complete cDNA contains the T7 RNA polymerase promoter site from the P1 primer. T7 RNA polymerase can now bind and intiate RNA synthesis, which is the amplification phase of the NASBA reaction.

Once the RNA is amplified using a primer pair as set forth above, detection of the amplificate or amplicon can be done using specific probes.

A probe that may be used for the detection of the amplificate generated using this primer set may comprise an oligonucleotide, 10–35 nucleotides in length comprising, at least a fragment of 10 nucleotides, of a sequence selected from the group consisting of:

5' TCG ATC GGA AGT AGT AAT ACT TTA 3' (OT2207) [SEQ ID NO:3]

5' TCG ATC GAA AGT AGT AAT ACT TTA 3' (pd95) [SEQ ID NO:4]

Probes comprising said sequence are also part of the present invention.

These preferred type-specific probes are complementary to a variable region (V1) of 16S ribosomal RNA. Surprisingly is found that these probes are type-specific. OT2207-probe is *M. pneumoniae* type 1 specific and pd 95-probe is *M. pneumoniae* type-2 specific.

The nucleotide sequence of the two *M. pneumoniae* strains revealed a one-point difference at the 16S rRNA level between *M. pneumoniae* type 1 and 2. This one-base difference in the variable region V1, consisted in a switch of the guanine base in *M. pneumoniae* type 1 by a adenine base in *M. pneumoniae* type 2 and was located at position 71 (numbering according to Weisburg et al., J. Bacteriol. 171:6455–6467 (1989)).

The present invention is not limited to the above-noted probes, which are only presented as type-specific examples. General (non-type-specific) Mycoplasmal 16S rRNA probes are known and, to the extent that they can bind to the amplified RNA, are included as useful in the detection of *M. pneumoniae* infection.

An oligonucleotide sequence used as detection-probe may be labeled with a detectable moiety. Various labeling moieties are known in the art. Said moiety may, for example, either be a radioactive compound, a detectable enzyme (e.g. horse radish peroxidase (HRP)) or any other moiety capable of generating a detectable signal such as a calorimetric, fluorescent, chemiluminescent or electro-chemiluminescent signal.

Such a detection probe can be used in a process for detection and typing of *M. pneumoniae* RNA, preferably 16 S rRNA, extracted directly from the sample and/or extracted from cultivated (sample-borne) *M. pneumoniae*.

An object of the present invention is directed to a process for amplifying a target ribonucleic acid in RNA of *Mycoplasma pneumoniae*, comprising the steps of:

(a) hybridizing to single-stranded ribosomal RNA a primer containing a polymerase promoter nucleic acid sequence and the sequence (P1) 5' AGG TCC TTT CAA CTT TGA TTC A 3' [SEQ ID NO:1];

(b) using reverse transcriptase to extend said first primer to thereby obtain an RNA-DNA hybrid, and creating a single-stranded DNA from said RNA-DNA hybrid;

(c) hybridizing to said single-stranded DNA a second primer consisting of the nucleic acid sequence (P2) 5' GAT CCT GGC TCA GGA TTA A 3' [SEQ ID NO:2] and extending said second primer to thereby obtain a double-stranded DNA template containing a functional polymerase promoter; and (d) using RNA polymerase to generate multiple copies of single-stranded RNA using said double-stranded DNA of step (c) as a template.

A preferred embodiment of the present invention is directed to the above process wherein the single stranded RNA obtained in step (d) acts as a template for the synthesis of (partial) double-stranded DNA by steps (a) through (c) with the primers annealing in reversed order, thereby establishing a cyclic phase of amplification (see FIG. 1).

Another preferred embodiment of the present invention is directed to the above process wherein step (b) RNase It activity is used to create single-stranded DNA from the RNA-DNA hybrid.

Another object of the present invention is directed to a method for the detection of *Mycoplasma pneumoniae* in a sample, comprising the steps of:

(a) hybridizing to the single-stranded ribosomal RNA a primer containing a polymerase promoter nucleic acid sequence and the sequence (P1) 5' AGG TCC TTT CAA CTT TGA TTC A 3' [SEQ ID NO:1];

(b) using reverse transcriptase to extend said first primer to thereby obtain an RNA-DNA hybrid, and creating a single-stranded DNA from said RNA-DNA hybrid, (c) hybridizing to said single-stranded DNA a second primer consisting essentially of the nucleic acid sequence (P2) 5' GAT CCT GGC TCA GGA TTA A 3' [SEQ ID NO:2] and extending said second primer to thereby obtain a double-stranded DNA template containing a functional polymerase promoter;

(d) using RNA polymerase to generate multiple copies of single-stranded RNA using said double-stranded DNA of step (c) as a template.

(e) hybridizing the RNA so amplified with the sequence specific oligonucleotide probe; and (f) detecting hybrids formed between said nucleic acid and said probe.

A preferred embodiment is directed to the above method wherein the sequence specific oligonucleotide probe of step (e) is type-specific.

Another preferred embodiment is directed to the above method wherein said type-specific oligonucleotide probe being 10–35 nucleotides in length and comprising, at least a fragment of 10 nucleotides of a sequence consisting of:

5' TCG ATC GGA AGT AGT AAT ACT TTA 3' (type 1) [SEQ ID NO: 3], or

5' TCG ATC GAA AGT AGT AAT ACT TTA 3' [SEQ ID NO:4] (type 2), or its complementary sequence.

Another object of the present invention is directed to a method for the detection of *Mycoplasma pneumoniae* in a sample, comprising the steps of:

(a) hybridizing RNA extracted from the sample and/or from cultivated sample-borne *M. pneumoniae* with one or more sequence specific probes; and (b) detecting hybrids formed between said nucleic acid and said probe(s).

Test kits for the detection of *M. pneumoniae* in clinical samples are also part of the present invention. A test kit according to the invention may comprise a set of primers according to the invention and a probe according to the invention. Such a test kit may additionally comprise suitable amplification reagents such as DNA and or RNA polymerases and mononucleotides.

An object of the present invention is directed to a test kit for detecting and optionally identifying *Mycoplasma pneumoniae* in a sample, wherein the kit comprises a pair of primers, wherein the first primer comprises an RNA polymerase promoter sequence and a hybridizing sequence being 10–35 nucleotides in length and comprising at least a fragment of 10 nucleotides of a sequence consisting of (P1) 5' AGG TCC TTT CAA TGA TTC A 3' [SEQ ID NO:1], and the second primer sequence being 10–35 nucleotides in length and comprising at least a fragment of 10 nucleotides of a sequence consisting of (P2) 5' GAT CCT GGC TCA GGA TTA A 3'.

Such a test kit may further comprise an oligonucleotide probe containing a nucleic acid sequence capable of hybridizing to the region of the RNA amplified using the first primer and the second primer.

A preferred object of the present invention is directed to a test kit typing *Mycoplasma pneumoniae* strains in a sample, wherein the kit comprises a pair of primers, wherein the first primer comprises an RNA polymerase promoter and a hybridizing sequence being 10–35 nucleotides in length and comprising at least a fragment of 10 nucleotides of a sequence consisting of (P1) 5' AGG TCC TTT CAA CTT TGA TTC A 3' [SEQ ID NO:6], and the second primer sequence being 10–35 nucleotides in length and comprising at least a fragment of 10 nucleotides of a sequence consisting of (P2) 5' GAT CCT GGC TCA GGA TTA A 3' [SEQ ID NO: 2], and further comprising an oligonucleotide probe being 10–35 nucleotides in length and comprising at least a fragment of 10 nucleotides of a sequence consisting of 5' TCG ATC GGA AGT AGT AAT ACT TTA 3' (type 1) [SEQ ID NO:3] or 5' TCG ATC GAA AGT AGT AAT ACT TTA 3' (type 2) [SEQ ID NO:4] which are capable of hybridizing to the region of the RNA amplified using the first primer and the second primer.

Another object of the present invention is directed to a test kit for detecting of *Mycoplasma pneumoniae* in a sample, wherein said test kit comprises:

one or more sequence specific oligonucleotide probes capable of hybridizing to RNA extracted from the sample and/or from cultivated sample-borne *M. pneumoniae*.

The invention is further exemplified by the following example

EXAMPLES

Example 1

Analysis of *M. pneumoniae* NA in clinical samples.

Bacterial strains

The 24 *M. pneumoniae* strains analyzed in this study are listed in Table 1. Fifteen strains were isolated from clinical samples in the Microbiology laboratory, University Hospital UIA, Belgium, during a study of respiratory tract infections in children between Oct. 1, 1991 and Mar. 31, 1992 and between Oct. 1, 1992 and Mar. 31, 1993 (Ieven et al., abstr. J127, p. 116. In Program and abstracts of the 34th Interscience Conference on Antimicrobial Agents and Chemotherapy. American Society for Microbiology, Washington (1994)).

In this study, nasopharyngeal aspirates of pediatric patients were examined for the presence of *M. pneumoniae* and respiratory viruses. The presence of *M. pneumoniae* was detected by culture and a PCR amplifying part of the P1 gene (Ursi et al., Acta Pathol. Microbiol.Immunol. Scand. 100:635–639 (1992)). The strains were isolated from 15 outpatients epidemiologically unrelated to each other. Three strains were Isolated in the United Kingdom between 1983 and 1986 (M 15/83, M 4/86, and M 510/86) and three strains in The Netherlands between 1970 and 1987 (P 635, P 71, and P 84). Three *M. pneumoniae* reference strains (FH, MAC, and PI 1428) were also included.

All *M. pneumoniae* strains were cultured in spiroplasma (SP4) broth as described previously (Ursi et al., J. Clin. Microbiol. 32:2873–2875 (1994)).

Nucleic acid isolation

Lysis and total nucleic acid isolation was performed using guanidinium thiocyanate-mediated cell lysis and adsorption of nucleic acid to silica particles (Boom et al., J. of Clin. Microbiology 28, 495–503 (1990)).

100 µl of SP4 broth with the bacteria was added to 900 µl of a guanidinium thiocyanate (GuSCN) lysis solution (5.25 M GuSCN, 50 mM Tris-HCl, pH 6.4, 20 mM EDTA, 1.3% (w/v) Triton X-100) and mixed vigorously for rapid lysis.

Subsequently, 70 µl of Hydrochloric acid-activated silicum dioxide particles [size-selected suspension of 1 mg/ml in 0.1 M Hydrochloric acid (Sigma); see ref. Boom et al., 1990] were added and the suspension was incubated during 10 minutes at room temperature with regular vortexing. Nucleic acid bound to the silica was spun down by centrifugation. Pelleted silica particles were washed twice with 1 ml GuSCN wash buffer [150 mM Tris-Hydrochloric acid (pH 6.4); 5.25 M Guanidinium thiocyanate], followed by two washing steps with 1 ml 70% ethanol and a single washing step with 1 ml acetone. After each washing step, the suspension was briefly centrifuged and the silica pellet was resuspended in the next washing solution by thorough mixing. After removal of the acetone, the silica particles were dried by incubation at 56° C. in a heating block during 10 minutes. Nucleic acid was eluted from the silica particles by incubation in 100 µl distilled water (RNase-/DNase-free H2O) at 56° C. during 10 minutes. Finally, the silica particles were spun down again and the supernatant was carefully pipetted into fresh reaction tubes avoiding any carry-over of silica. Extracted nucleic acid samples were stored at −70° C. until use.

Primers and probes

The primers and probes used are listed in Table 2.

Synthesis of primers and probes:

All oligonucleotide primers and probes were synthesized on a PCR-MATE 391 DNA synthesizer (Applied Biosystems) using phosphoramidite biochemistry. Oligonucleotides for ELGA detection (see below) were synthesized with a 5'-amino link (Aminolink 2; Applied Biosystems) for subsequent coupling of Horse Radish Peroxidase (HRP).

Amplification primers were purified by electrophoretically separating the crude oligonucleotide solutions over a 20% polyacrylamide/7M Urea slabgel and subsequent elution of the full-length oligonucleotide from the corresponding gel band. After elution from the gel slices and concentration by ethanol precipitation, primers were dissolved in Milli-Q water and concentrations determined by OD(260 nm) measurement.

Detection probes were conjugated with HRP (Boehringer) by coupling the enzyme to the amino link of the oligonucleotide using the cross-linking reagents SDPD (Pharmacia) and EMCS (Fluka). Unbound HRP was removed over a Qiagen Tip-100 column (Qiagen). The HRP-labeled oligonucleotides were purified by polyacrylamide gel electrophoresis and subsequent elution of the HRP-oligonucleotides from the gel slices by overnight incubation in water. The amount of HRP-conjugated oligonucleotide was calculated from OD(260 nm) and OD(400 nm) measurement. The solutions were stored at −70° C.

Selection of primers and probes:

The primers and probes used (Table 2) were chosen from a 16S rRNA sequence alignment of Mycoplasma species (Weisburg el at., J. Bacteriol. 171:6455–6467 (1989))). Forward primer OT2156 was chosen from a highly conserved region, while reverse primer OT2157 was localized on the variable region V2 (Neefs et al., Nucleic Acids Res. 18 suppl:2237–2317 (1990)). These primers were calculated to be 190 nucleotides apart. This stretch contains a sequence specific for M. pneumoniae. Type-specific probes complementary to the variable region V1 of the 16S rRNA gene were synthesized for the identification of M. pneumoniae type 1 (OT2207) and M. pneumoniae type 2 (pd 95).

NASBA amplification

The NASBA reactions were performed as described by Kievits et al. (J. Virol. Methods. 35:273–286 (1991)) with some modifications. The final volume of the reaction mixture was 20 µl. First, to a 10-µl volume of prereaction mixture consisting of 40 mM Tris-HCl, pH 8.5, 12 mM MgCl$_2$, 70 mM KCl, 5 mM DTT, 1 mM of each dNTP, 2 mM ATP, 2 mM CTP, 2 mM UTP, 1.5 mM GTP, 0.5 mM ITP, 15% (v/v) DMSO, 0.2 µM of each primer, was added. After addition of 5 µl of target RNA the tubes were incubated for 5 min at 65° C. to uncoil the tertiary and secondary structures of the 16S rRNA. The reaction mixtures were then transferred to 41° C. for 5 min. Finally, 5 µl of enzyme mix was added, containing 1.5 M sorbitol, 2.1 µg bovine serum albumin (Boehringer Mannheim), 32 U T7 RNA polymerase (Pharmacia), 6.4 U AMV-RT (Seikagaku), 0.08 U RNase-H (Pharmacia), resulting in a final volume of 20 µl. Isothermal amplification of the target RNA was performed at 41°C. for 1.5 h. Reaction mixtures in which the target nucleic acid was replaced by 5 µl RNase-/DNase-free H$_2$O, served as negative controls. The amplification products were processed immediately by the ELGA.

Analysis of NASBA-amplified products (ELGA)

NASBA products were identified by a rapid, non-radioactive, 'in-solution' hybridization assay (ELGA) with species-specific oligonucleotide probes 5'-labelled with horse-radish peroxidase (HRP). Since the NASBA products are single-stranded RNA there is no need for prior denaturation. After hybridization, excess non-hybridized ELGA probes were separated from the homologous hybridized product by vertical gel electrophoresis and visualized in the acrylamide gel by incubating the gel in the substrate solution for HRP. Because of its lower mobility, the homologous hybridized product migrates in the gel above the free ELGA probe.

One µl of the NASBA reaction product was mixed with 4 µl hybridization solution (final concentration of this reaction mix was 1×SSC (0.15 M NaCl, 0.015 M sodium citrate), 0.01% bromophenol blue, 0.01% xylene cyanol and 6.10$^{11}$ molecules of HRP-labelled probes) and incubated at 50° C. for 15 min. Hybridization reaction mixtures (2.5 µl ) were then applied on a 7% acrylamide gel, containing 0.04% (w/v) dextran sulphate. After electrophoresis, the gel was incubated in 40 ml of substrate solution (0.125 mg of 3,3',5,5'-tetramethylbenzidine per ml, 0.003% (v/v) H$_2$O$_2$ in 0.1 M sodium citrate, pH 5.6) for approximately 5 min at room temperature. The gel was fixed by incubation in 50% (v/v) methanol overnight at room temperature.

Sequencing of the NASBA amplicons

For the sequencing of the NASBA amplicons (−RNA) the template was separated from the primers and free nucleotides. This was done by purifying 10 µl of amplicon over a QIAquick-spin column (QIAquick-spin, PCR Purification Kit (250), Qiagen), according to the manufacturer's instructions. For nucleotide sequence analysis, 1/10 of the purified sample was used, as well as 1.6 pmol of 5'-end [32] P-labelled primer 2 (OT2156, Table 2). Nucleotide sequence analysis was performed with the dideoxynucleotide-terminated chain elongation method, modified for the use of RT and RNA templates (Lane et al., Proc. Natl. Acad. Sci. USA 82:6955–6959 (1985))

TABLE 1

*M. pneumoniae strains used in this study*

| Nr. | Strain | Source[a] | Year and source of isolation | Clinical picture | Type[b] |
|---|---|---|---|---|---|
| 1 | FH (NCTC 10119) | NCTC | 1959; not specified | Pneumonia | 2 |
| 2 | M 15/83 | NCTC | 1983; sputum | Pneumonia | 1 |
| 3 | M414/86 | NCTC | 1986; sputum | Pneumonia | 1 |
| 4 | M510/86 | NCTC | 1986; sputum | Pneumonia | 1 |
| 5 | P635 | RIVM | 1970's; throat swab | Pneumonia | 2 |
| 6 | P71 | RIVM | 1987; BAL | Pneumonia | 1 |
| 7 | P84 | RIVM | 1973; not specified | Pneumonia | 2 |
| 8 | M2117350 | UZA | 1992; NPA[d] | Acute bronchitis | 1 |
| 9 | M2107084 | UZA | 1992; throat swab | Acute bronchitis Erythema multiforma | 1 |
| 10 | M2117245 | UZA | 1992; NPA | URTI[e] | 1 |
| 11 | M2107079 | UZA | 1992; sputum | Acute lobar pneumonia | 1 |
| 12 | M2107374 | UZA | 1992; NPA | Acute lobar pneumonia | 1 |
| 13 | M2117235 | UZA | 1992; throat swab | Acute lobar pneumonia | 1 |
| 14 | M2117430 | UZA | 1992; NPA | Acute bronchitis | 1 |
| 15 | M3057031 | UZA | 1993; NPA | Acute bronchitis | 1 |
| 16 | M3037439 | UZA | 1993; NPA | Acute bronchopneumonia | 1 |
| 17 | 21C86 | UZA | 1992; NPA | Acute bronchitis | 1 |
| 18 | 21K11 | UZA | 1992; NPA | Acute bronchopneumonia | 2 |
| 19 | 21K33 | UZA | 1992; NPA | Acute bronchopneumonia | 1 |
| 20 | 21G93 | UZA | 1992; NPA | Acute bronchopneumonia | 1 |
| 21 | 21I105 | UZA | 1992; sputum | Acute bronchopneumonia Exanthema | 1 |
| 22 | DEV | UZA | 1991; NPA | Acute bronchopneumonia Erythema multiforma | 1 |
| 23 | PI1428 | (ATCC ATCC 29085) | 1964; throat swab | Pneumonia | 1 |
| 24 | MAC | (ATCC ATCC 15492) | 1944; lung tissue | Not specified | 2 |

[a]Abbreviations: NCTC, National Collection of Type Cultures, Central Public Health Laboratory, London, United Kingdom; ATCC, American Type Culture Collection, Rockville, Md.; RIVM, Rijksinstituut voor Volksgezondheid en Milieuhygiëne, Bilthoven, The Netherlands; UZA, Universitair Ziekenhuis Antwerpen, Edegem, Belgium.
[b]Typing results were obtained with NASBA as described in this study.
[c]BAL, bronchoalveolar lavage.
[d]NPA, nasopharyngeal aspirate.
[e]URTI, upper respiratory tract infection.

TABLE 2

Sequences of primers and probes used in amplification of 16S rRNA

| Oligo | Sequence | |
|---|---|---|
| P1 OT2157 | 5' AAT TCT AAT ACG ACT CAC TAT AGG GAG GTC CTT TCA ACT TTG ATT CA 3' | [SEQ ID NO:5] |
| P2 OT2156 | 5' GAT CCT GGC TCA GGA TTA A 3' | [SEQ ID NO:2] |
| type 1: OT2207 | 5' TCG ATC GGA AGT AGT AAT ACT TTA 3' | [SEQ ID NO:3] |
| type 2: pd 95 | 5' TCG ATC GAA AGT AGT AAT ACT TTA 3' | [SEQ ID NO:4] |

Primers OT2156 and OT2157 were used for NASBA amplification. Probes OT2207 and pd 95 were used for typing the 24 *M. pneumoniae* strains.

Figure 1:
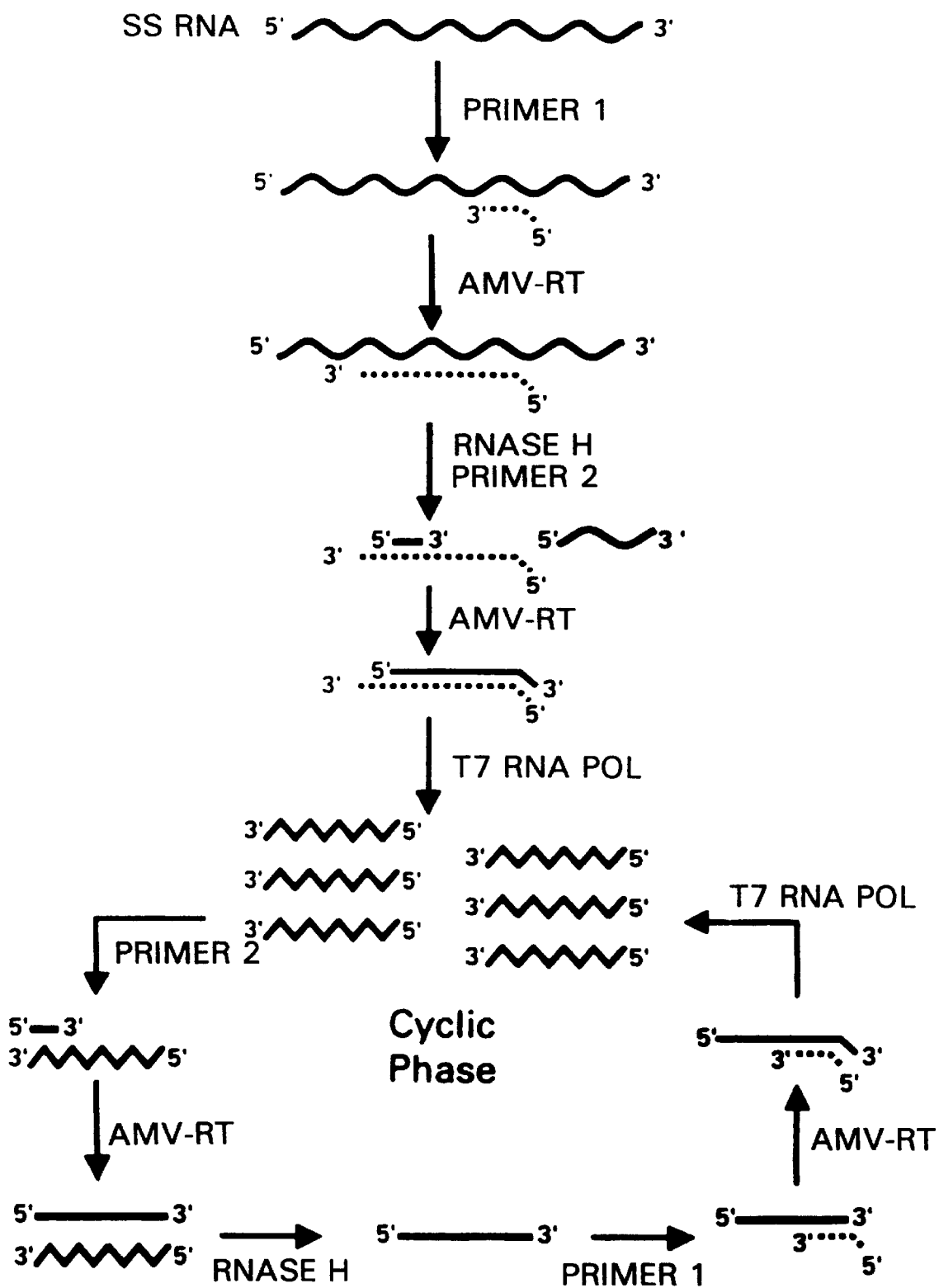
FIG. 1: The NASBA amplification principle. Sense RNA 5'∿∿∿3'Sense DNA 5'———3'Antisense RNA 3'∿∿∿5'Antisense DNA3'········5'
Figure 2A:
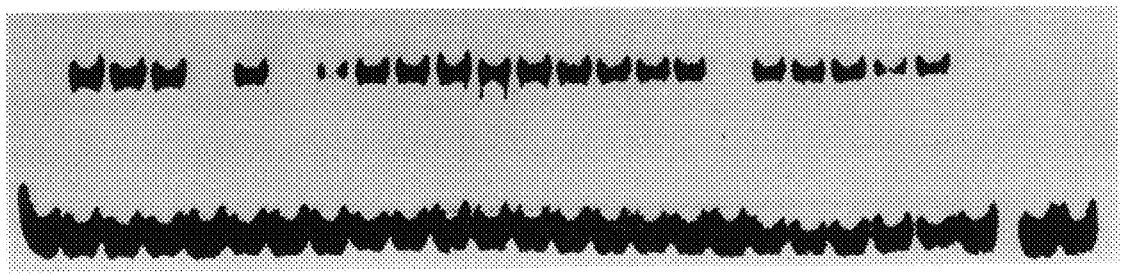
FIG. 2a and 2b: The specificity of NASBA in combination with ELGA for typing a collection of 24 *M. pneumoniae* strains is shown.
Figure 2B:
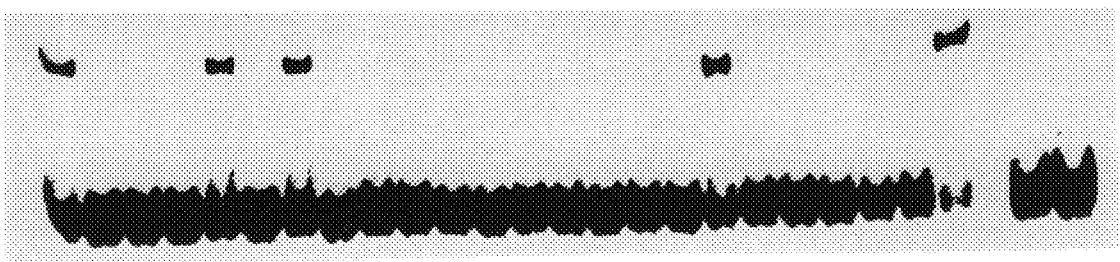

Probe OT2207 (specific for type 1) hybridized with amplified RNA from 19 of the 24 strains (FIG. 2a) and probe pd 95 (specific for type 2) hybridized with amplified RNA from the remaining 5 strains (FIG. 2b) (Table 1).

What is claimed is:

1. A pair of oligonucleotide primers for the amplification of *Mycoplasma pneumoniae* nucleic acid, comprising oligonucleotides containing the following nucleic acid sequences:

(P1) 5' AGG TCC TTT CAA CTT TGA TTC A 3' (SEQ ID NO:1), (P2) 5' GAT CCT GGC TCA GGA TTA A 3' (SEQ ID NO:2), one of which is covalently bonded to a promoter nucleic acid sequence.

2. A method for amplifying a target ribonucleic acid in RNA of *Mycoplasma pneumoniae*, comprising the steps of:

(a) hybridizing to single-stranded ribosomal RNA a primer containing a polymerase promoter nucleic acid sequence and the sequence (P1) 5' AGG TCC TTT CAA CTT TGA TTC A 3' (SEQ ID NO:1);

(b) using reverse transcriptase to extend said first primer to thereby obtain an RNA-DNA hybrid, and creating a single-stranded DNA from said RNA-DNA hybrid;

(c) hybridizing to said single-stranded DNA a second primer containing the sequence (P2) 5' GAT CCT GGC TCA GGA TTA A 3' (SEQ ID NO:2) and extending said second primer to thereby obtain a double-stranded DNA template containing a functional polymerase promoter; and (d) using RNA polymerase to generate multiple copies of single-stranded RNA using said double-stranded DNA of step (c) as a template.

3. The method according to claim 2, wherein the single stranded RNA obtained in step (d) acts as a template for the synthesis of partial double-stranded DNA by steps (a) through (c) with the primers annealing in reversed order, thereby establishing a cyclic phase of amplification.

4. The method according to claim 2, wherein in step (b) RNase H activity is used to create single-stranded DNA from the RNA-DNA hybrid.

5. A method for the detection of *Mycoplasma pneumoniae* in a sample, comprising the steps of:

(a) hybridizing to single-stranded ribosomal RNA a primer containing a polymerase promoter nucleic acid sequence and the sequence (P1) 5' AGG TCC TTT CAA CTT TGA TTC A 3' (SEQ ID NO:1);

(b) using reverse transcriptase to extend said first primer to thereby obtain an RNA-DNA hybrid, and creating a single-stranded DNA from said RNA-DNA hybrid;

(c) hybridizing to said single-stranded DNA a second primer containing the sequence (P2) 5' GAT CCT GGC TCA GGA TTA A 3' (SEQ ID NO:2) and extending said second primer to thereby obtain a double-stranded DNA template containing a functional polymerase promoter;

(d) using RNA polymerase to generate multiple copies of single-stranded RNA using said double-stranded DNA of step (c) as a template;

(e) hybridizing the RNA so amplified with a sequence specific oligonucleotide probe; and (f) detecting hybrids formed between said nucleic acid and said probe.

6. The method according to claim 5, wherein the sequence specific oligonucleotide probe of step (e) is type-specific.

7. The method according to claim 6, wherein said type-specific oligonucleotide probe is 10–35 nucleotides in length and comprises at least a fragment of 10 nucleotides of a sequence selected from the group consisting of:

5' TCG ATC GAA AGT AGT AAT ACT TTA 3' (type 1) (SEQ ID NO:3), 5' TCG ATC GAA AGT AGT AAT ACT TTA 3' (type 2) (SEQ ID NO:4), and their complementary sequences.

8. A kit for detecting and optionally identifying *Mycoplasma pneumoniae* in a sample, wherein the kit comprises a pair of primers, wherein the first primer comprises an RNA polymerase promoter sequence and a hybridizing sequence of 10–35 nucleotides in length comprising at least a fragment of 10 nucleotides of the sequence (P1) 5' AGG TCC TTT CAA CTT TGA TTC A 3' (SEQ ID NO:1), and the second primer comprises a hybridizing sequence of 10–35 nucleotides in length comprising at least a fragment of 10 nucleotides of the sequence (P2) 5' GAT CCT GGC TCA GGA TTA A 3' (SEQ ID NO:2).

9. The kit according to claim 8, further comprising an oligonucleotide probe containing a nucleic acid sequence capable of hybridizing to the region of the RNA amplified using the first primer and the second primer.

10. A kit for typing *Mycoplasma pneumoniae* strains in a sample, wherein the kit comprises a pair of primers, the first primer comprising an RNA polymerase promoter nucleic acid sequence and a hybridizing sequence of 10–35 nucleotides in length comprising at least a fragment of 10 nucleotides of the oligonucleotide (P1) 5' AGG TCC TTT CAA CTT TGA TTC A 3', (SEQ ID NO:1), and the second primer comprising a hybridizing sequence of 10–35 nucleotides in length comprising at least a fragment of 10 nucleotides of the oligonucleotide (P2) 5' GAT CCT GGC TCA GGA TTA A 3' (SEQ ID NO:2), said kit further comprising an oligonucleotide probe of 10–35 nucleotides in length comprising at least a fragment of 10 nucleotides of the oligonucleotide selected from the group consisting of 5' TCG ATC GGA AGT AGT AAT ACT TTA 3' (type 1) (SEQ ID NO:3) and 5' TCG ATC GAA AGT AGT AAT ACT TTA 3' (type 2) (SEQ ID NO:4), which is capable of hybridizing to the region of the RNA amplified using the first primer and the second primer.

11. An oligonucleotide, 10–35 nucleotides in length, comprising at least a fragment of 10 nucleotides of a sequence selected from the group consisting of:

(P1) 5' AGG TCC TTT CAA CTT TGA TTC A 3' (SEQ ID NO:1), (P2) 5' GAT CCT GGC TCA GGA TTA A 3' (SEQ ID NO:2), and their complementary sequences, said oligonucleotide covalently bonded to a promoter nucleic acid sequence.

12. An oligonucleotide, 10–35 nucleotides in length, comprising a sequence selected from the group consisting of:

(P1) 5' AGG TCC TTT CAA CTT TGA TTC A 3' (SEQ ID NO:1), (P2) 5' GAT CCT GGC TCA GGA TTA A 3' (SEQ ID NO:2), and their complementary sequences, said oligonucleotide covalently bonded to a promoter nucleic acid sequence.

13. A method for amplifying a target ribonucleic acid in RNA of *Mycoplasma pneumoniae*, comprising the steps of:

(a) hybridizing to single-stranded ribosomal RNA a primer containing a polymerase promoter nucleic acid sequence and a sequence, 10–35 nucleotides in length, comprising at least 10 consecutive nucleotides of the sequence (P1) 5' AGG TCC TTT CAA CTT TGA TTC A 3' (SEQ ID NO:1);

(b) using reverse transcriptase to extend said first primer to thereby obtain an RNA-DNA hybrid, and creating a single-stranded DNA from said RNA-DNA hybrid;

(c) hybridizing to said single-stranded DNA a second primer containing a sequence, 10–35 nucleotides in length, comprising at least 10 consecutive nucleotides of the sequence (P2) 5' GAT CCT GGC TCA GGA TTA A 3' (SEQ ID NO:2), and extending said second primer to thereby obtain a double-stranded DNA template containing a functional polymerase promoter; and (d) using RNA polymerase to generate multiple copies of single-stranded RNA using said double-stranded DNA of step (c) as a template.

14. The method according to claim 13, wherein the single stranded RNA obtained in step (d) acts as a template for the synthesis of partial double-stranded DNA by steps (a) through (c) with the primers annealing in reversed order, thereby establishing a cyclic phase of amplification.

15. The method according to any of claims 13–14, wherein step in (b) RNase H activity is used to create single-stranded DNA from the RNA-DNA hybrid.

16. A method for the detection of *Mycoplasma pneumoniae* in a sample, comprising the steps of:

(a) hybridizing to the single-stranded ribosomal RNA a primer containing a polymerase promoter nucleic acid sequence and a sequence, 10–35 nucleotides in length, comprising at least 10 consecutive nucleotides of the sequence (P1) 5' AGG TCC TTT CAA CTT TGA TTC A 3' (SEQ ID NO:1);

(b) using reverse transcriptase to extend said first primer to thereby obtain an RNA-DNA hybrid, and creating a single-stranded DNA from said RNA-DNA hybrid;

(c) hybridizing to said single-stranded DNA a second primer containing a sequence, 10–35 nucleotides in length, comprising at least 10 consecutive nucleotides of the sequence (P2) 5' GAT CCT GGC TCA GGA TTA A 3' (SEQ ID NO:2), and extending said second primer to thereby obtain a double-stranded DNA template containing a functional polymerase promoter;

(d) using RNA polymerase to generate multiple copies of single-stranded RNA using said double-stranded DNA of step (c) as a template;

(e) hybridizing the RNA so amplified with a sequence specific oligonucleotide probe; and (f) detecting hybrids formed between said nucleic acid and said probe.

17. The method according to claim 16, wherein the sequence specific oligonucleotide probe of step (e) is type-specific.

18. The method according to claim 17, wherein said type-specific oligonucleotide probe is 10–35 nucleotides in length and comprises at least a fragment of 10 nucleotides of a sequence selected from the group consisting of:

5' TCG ATC GGA AGT AGT AAT ACT TTA 3' (type 1) (SEQ ID NO:3),

5' TCG ATC GAA AGT AGT AAT ACT TTA 3' (type 2) (SEQ ID NO:4), and their complementary sequences.

19. A method for the detection of RNA of *Mycoplasma pneumoniae* in a sample, comprising the steps of:

a) obtaining a sample which may contain RNA of *Mycoplasma pneumoniae;* b) performing isothermal transcription based amplification on the sample with two oligonucleotide primers, a first primer which is 10–35 nucleotides in length and comprises at least 10 consecutive nucleotides of SEQ ID NO:1; and a second primer which is 10–35 nucleotides in length and comprises at least 10 consecutive nucleotides of SEQ ID NO:2; and c) detecting the resulting product of step b) whereby detection of the amplification product indicates the presence of RNA of *Mycoplasma pneumoniae* in the sample.

20. The method of claim 19, wherein said detection of the amplification product uses an oligonucleotide probe of 10–35 nucleotides in length comprising at least 10 consecutive nucleotides of a sequence selected from the group consisting of SEQ ID NO:3 and SEQ ID NO:4.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: MYCOPLASMA PNEUMONIAE

<400> SEQUENCE: 1
aggtcctttc aactttgatt ca                                    22

<210> SEQ ID NO 2
<211> LENGTH: 19
<212> TYPE: DNA
<213> ORGANISM: MYCOPLASMA PNEUMONIAE

<400> SEQUENCE: 2
gatcctggct caggattaa                                        19

<210> SEQ ID NO 3
<211> LENGTH: 24
<212> TYPE: DNA
<213> ORGANISM: MYCOPLASMA PNEUMONIAE

<400> SEQUENCE: 3
tcgatcggaa gtagtaatac ttta                                  24

<210> SEQ ID NO 4
<211> LENGTH: 24
<212> TYPE: DNA
<213> ORGANISM: MYCOPLASMA PNEUMONIAE

<400> SEQUENCE: 4
tcgatcgaaa gtagtaatac ttta                                  24

<210> SEQ ID NO 5
<211> LENGTH: 47
<212> TYPE: DNA
<213> ORGANISM: MYCOPLASMA PNEUMONIAE

<400> SEQUENCE: 5
aattctaata cgactcacta tagggaggtc ctttcaactt tgattca         47

<210> SEQ ID NO 6
<211> LENGTH: 25
<212> TYPE: DNA
<213> ORGANISM: BACTERIOPHAGE T7

<400> SEQUENCE: 6
aattctaata cgactcacta taggg                                 25